United States Patent
Paliwal et al.

(10) Patent No.: US 7,688,938 B2
(45) Date of Patent: Mar. 30, 2010

(54) METHOD AND APPARATUS FOR LOW DOSE COMPUTED TOMOGRAPHY

(75) Inventors: Bhudatt R. Paliwal, Madison, WI (US); Robert Jeraj, Madison, WI (US); Ke Sheng, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 239 days.

(21) Appl. No.: 11/814,985

(22) PCT Filed: Jan. 22, 2007

(86) PCT No.: PCT/US2007/001732

§ 371 (c)(1),
(2), (4) Date: Jul. 27, 2007

(87) PCT Pub. No.: WO2007/084789

PCT Pub. Date: Jul. 26, 2007

(65) Prior Publication Data

US 2008/0152075 A1    Jun. 26, 2008

Related U.S. Application Data

(60) Provisional application No. 60/760,896, filed on Jan. 20, 2006.

(51) Int. Cl.
*A61B 6/03* (2006.01)
(52) U.S. Cl. ........................................................ 378/16
(58) Field of Classification Search ..................... 378/4, 378/9, 16, 19, 65
See application file for complete search history.

(56) References Cited

U.S. PATENT DOCUMENTS

| | | | |
|---|---|---|---|
| 4,878,169 A | 10/1989 | Toner et al. | |
| 5,379,333 A | 1/1995 | Toth | |
| 5,548,627 A * | 8/1996 | Swerdloff et al. | 378/4 |
| 6,490,337 B1 | 12/2002 | Nagaoka et al. | |
| 6,618,467 B1 | 9/2003 | Ruchala et al. | |
| 6,810,102 B2 | 10/2004 | Hsieh et al. | |
| 6,914,959 B2 * | 7/2005 | Bailey et al. | 378/65 |
| 7,254,209 B2 * | 8/2007 | Zhao et al. | 378/4 |
| 2003/0048868 A1 | 3/2003 | Bailey et al. | |
| 2005/0185759 A1 | 8/2005 | Toth et al. | |

FOREIGN PATENT DOCUMENTS

EP        1 429 588 A2    6/2004

(Continued)

OTHER PUBLICATIONS

Kalender, Willi A., et al, Dose Reduction in CT by Anatomically Adapted Tube Current Modulation. II. Phantom Measurements., Nov. 1, 1999, vol. 26, No. 11 pp. 2248-2253. Medical Physics, AIP, Melville, NN, USA.

(Continued)

*Primary Examiner*—Chih-Cheng G Kao
(74) *Attorney, Agent, or Firm*—Boyle Fredrickson, S.C.

(57) ABSTRACT

A computed tomography machine (1) provides for improved dose efficiency by calculating an optimized set of beam intensities to produce the desired image quality. Determination of the beam weights is based on an a priori modeling (53) of the properties of the patient being imaged.

27 Claims, 3 Drawing Sheets

FOREIGN PATENT DOCUMENTS

WO  WO 2004/080309 A2  9/2004
WO  WO 2005/099577 A1  10/2005

OTHER PUBLICATIONS

Ke Sheng, et al., Imaging Dose Management Using Multi-resolution in CT-guided Radiation Therapy; Imaging Dose Management Using Multi-Resolution in CT-guided Radiation Therapy, Physics in Medicine and Biology, Mar. 21, 2005, vol. 50, No. 6, pp. 1205-1219, Taylor and Francis Ltd., London, Great Britain.

Möhrs, Sascha, Supplementary European Search Report, European Patent Office, Nov. 24, 2009, The Hague, The Netherlands.

* cited by examiner

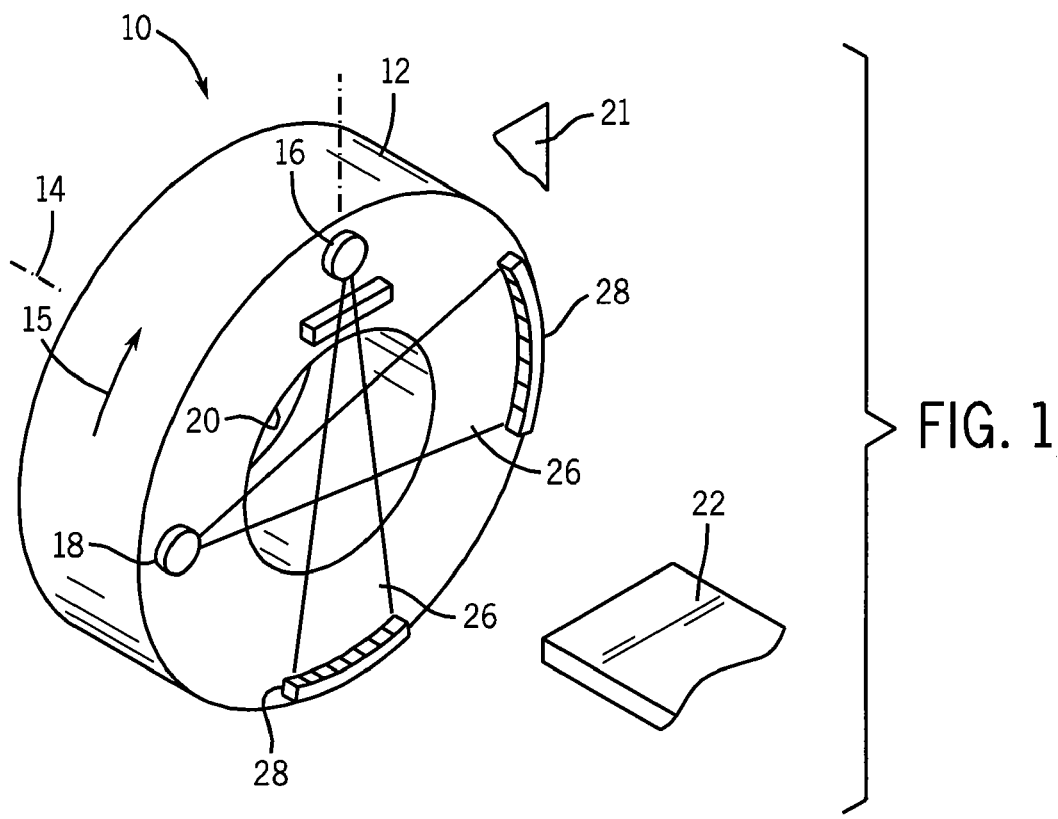
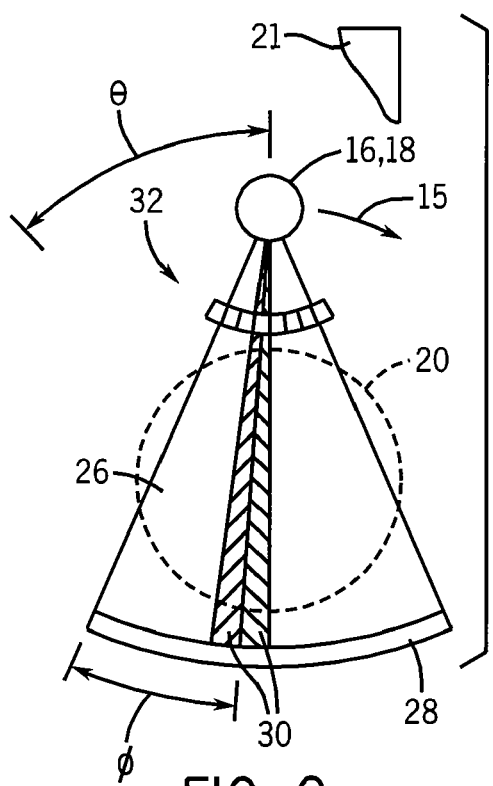
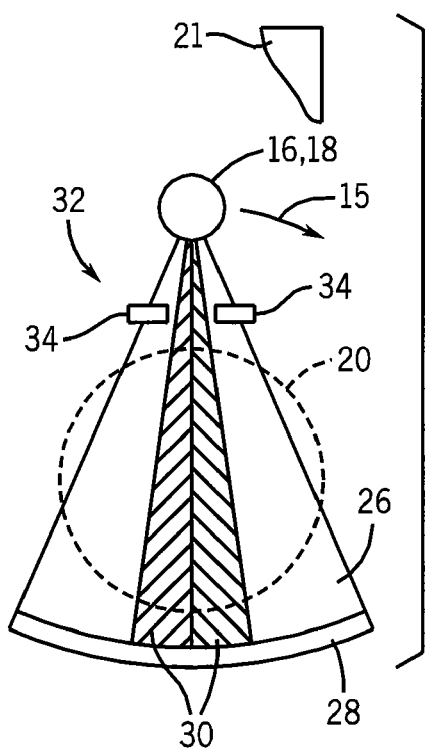
FIG. 1
FIG. 2
FIG. 3

METHOD AND APPARATUS FOR LOW DOSE COMPUTED TOMOGRAPHY

CROSS REFERENCE TO RELATED APPLICATION

This application is a PCT application and claims priority to Provisional Patent Application Ser. No. 60/760,896, filed on Jan. 20, 2006, titled Partial Volume Imaging Using Portal Images, the disclosure of which is incorporated herein by reference.

BACKGROUND OF THE INVENTION

The present invention relates to computed tomography machines that are free-standing or that are part of a radiation therapy machine, and in particular to a computed tomography machine providing a reduced dose to the patient.

External-source radiation therapy uses a radiation source that is external to the patient, typically either a radioisotope or a megavoltage energy x-ray source, such as a linear accelerator. The external source produces a collimated radiation beam directed along an axis of radiation toward a tumor site. The adverse effect of irradiating healthy tissue may be reduced, while maintaining a given dose of radiation in the tumorous tissue, by projecting the radiation beam into the patient along a variety of radiation axes with the beams converging on the tumor site.

Intensity modulated radiation therapy (IMRT) provides an external beam of radiation composed of individually intensity-modulated "beamlets". The intensities or weights of the beamlets are calculated to provide a desired dose pattern of radiation for an arbitrary shaped tumor within the patient while minimizing radiation in other areas. One such system, commercially available from TomoTherapy, Inc. of Madison, Wis., provides a radiation source that rotates about the patient on a helical line producing a fan beam of multiple beamlets, each beamlet controlled by a movable shutter.

With the increased accuracy possible with IMRT, the problem arises of obtaining precise knowledge of the position, shape, and size of the target which often changes between the time that the treatment plan was developed and the actual treatment time. In image guided radiation therapy (IGRT), the target geometry is monitored at the time of radiation treatment so that the treatment plan may be adjusted accordingly. Ideally, the imaging system used for this purpose is computer tomography (CT) which can provide precise three-dimensional imaging of a target needed for maximizing the benefit of IMRT.

One method of providing IGRT with CT is to provide a rail system to transfer the patient between an adjacent CT and the IMRT machines. Alternatively, a CT machine may be incorporated into the IMRT machine itself, either by adding a kilovoltage x-ray source and detector, or by using the radiation therapy megavoltage source and adding megavoltage detector.

Generally, this latter approach of megavoltage CT (MVCT) requires high imaging doses because of the penetrating nature of megavoltage beams, low detector efficiency and the need to repeat imaging on a daily basis for patient positioning. A common strategy to reduce the exposure to the patient in MVCT is to reduce the area of the imaging, for example, by limiting radiation principally to the treatment area, this latter option making dual use of the radiation for both treatment and imaging. Unfortunately, reduction of the exposure area in CT creates "partial volume" artifacts in the reconstructed image. These artifacts are caused by structure outside of the image area which affects the measurements of the image region to the extent that radiation passes through this outside structure to reach the image area. Because the outside structure is not fully characterized by imaging, its attenuating influence is not fully cancelled, and the result is streaks in the image.

U.S. Pat. No. 6,618,467 issued Sep. 9, 2003, assigned to the assignee of the present invention, and hereby incorporated by reference, describes an MVCT system that addresses this problem of partial volume artifacts by performing a pre-scan of an entire patient slice with low flux radiation to obtain a low resolution measurement of the outside structure. This low flux scan is combined with the radiation used during the treatment to provide images with reduced partial volume artifacts.

Alternative methods of dealing with the partial volume artifacts are described for example, in U.S. Pat. No. 4,878,169 issued Oct. 31, 1989, and U.S. Pat. No. 6,810,102 issued Oct. 26, 2004, which also augment CT projection data taken of a limited region of interest with full slice projection data obtained at a different time.

SUMMARY OF THE INVENTION

The present inventors have recognized that minimizing the region of exposure does not necessarily optimize the imaging dose for a given quality of image. The contribution of each measuring radiation beamlet to the quality of the resultant tomographic image varies significantly as a complex function of the internal structure of the patient being imaged.

Generally, the structure of the patient being imaged is unknown, however, the present inventors have determined that in many cases there will be sufficient a priori knowledge about the patient, for example, when the images are part of a sequence of images, when there is a planning image, or when the internal structure of the patient conforms to standard patterns. In these cases, the a priori knowledge about the patient may be used to intelligently select beamlets according to their contribution to image quality and thereby effect an arbitrary trade-off between dose and image quality. Generally, for a given image quality, the dose may be reduced from what would be required if uniform exposures across beamlets are used.

Specifically then, the present invention provides a computed tomography imaging machine that includes a radiation source providing a radiation beam divisible into beamlets each being individually controllable in intensity. A radiation detector receives and measures these beamlets after they have passed through a patient held on a patient support between the radiation source and radiation detector. A controller holds a stored model of the patient and using the stored model, determines and controls the intensity of the radiation beam in the beamlets based on a calculated contribution by the beamlet to a quality of a tomographic image.

Thus it is one aspect of at least one embodiment of the invention to provide a computed tomography machine providing sophisticated control of the intensity of individual beamlets to precisely tailor the radiation dose to a desired image quality.

The determination of the intensity of the radiation beams may be performed by an inverse calculation in which intensities are iteratively modified based on a comparison between a calculated image using the stored model and the stored model itself.

It is thus another aspect of at least one embodiment of the invention to provide a beamlet analysis technique that is applicable to a wide variety of different images.

The intensity of the radiation beam in the regions may controlled to reduce dose to the patient for a given image quality.

It is thus another aspect of at least one embodiment of the invention to significantly decrease dose to a patient for CT imaging.

The stored model may be a tomographic image of the patient.

It is thus another aspect of at least one embodiment of the invention to provide a system that may create a stored model from automatically acquired data without the need for manual construction of a model of the patient.

The tomographic image may be a previous image of the patient provided by the computed tomography imaging machine.

It is another aspect of at least one embodiment of the invention to provide a system that may significantly decrease dose in CT cinematography.

The previous image may be obtained with the controller controlling the intensity of the regions of the radiation beam.

It is thus another aspect of at least one embodiment of the invention to allow the system to make use of its own optimized images for the purpose of optimizing future images.

The radiation source may be kilovoltage x-ray sources and/or megavoltage x-ray sources.

It is another aspect of at least one embodiment of the invention that it may work with either radiation therapy systems, combined radiation therapy machines and CT machines, or stand-alone CT systems where it is desired to control the dose.

The radiation source may be a multi-leaf collimator providing a plurality of leaves moving into and out of the radiation beam to control the intensity within the regions wherein one leaf is associated with each region.

It is thus another aspect of at least one embodiment of the invention to provide a simple mechanism for independently controlling the beamlets of a CT system.

Alternatively, the radiation source may include opposing shutter blades moving across multiple regions to control the intensity within the regions.

It is another aspect of at least one embodiment of the invention to provide a system that may work broadly with other forms of beam intensity control.

The controller may control the intensity of the radiation beams assuming a precondition of a subset of regions of given intensity.

It is another aspect of at least one embodiment of the invention to provide a system that may work with equipment providing limited control of beam intensities.

The subset of regions of given intensity may be obtained from a radiation therapy treatment plan.

It is another aspect of at least one embodiment of the invention to provide a system that can work with a predefined radiation plan, and hence a set of predefined beamlets, to reduce additional exposure to the patient.

The intensity of the beamlets may be controlled to on or off states or among a range of intensities.

It is an aspect of the present invention that it may work with a range of different types of beamlet modulation systems.

The computed tomography imaging machine may include multiple radiation sources and wherein the radiation beam is provided by no less than one radiation source.

It is another aspect of at least one embodiment of the invention that it may work with computed tomography machines having multiple radiation sources so long as one of the radiation sources or the combination of the multiple radiation sources provides for control of the beamlet weights.

The controller further may reconstruct a tomographic image from the attenuation signals from the controlled intensity radiation beams after augmenting the attenuation signals with information from the model.

It is another aspect of at least one embodiment of the invention that it may be used in combination with other methods of reducing partial volume artifacts.

These particular objects and advantages may apply to only some embodiments falling within the claims and thus do not define the scope of the invention.

BRIEF DESCRIPTION OF THE DRAWINGS

FIG. 1 is a fragmentary perspective view of a simplified computed tomography machine having multiple radiation sources for rotation about a patient support;

FIG. 2 is a schematic representation of one of the sources of FIG. 1 showing the opposed radiation source and detector together with a duty-cycle modulating shutter system such as controls the intensity of individual beamlets of a radiation beam;

FIG. 3 is a figure similar to that of FIG. 2 showing an alternative shutter system with continuously positionable collimator blades;

DETAILED DESCRIPTION OF THE PREFERRED EMBODIMENT

Figure 4:
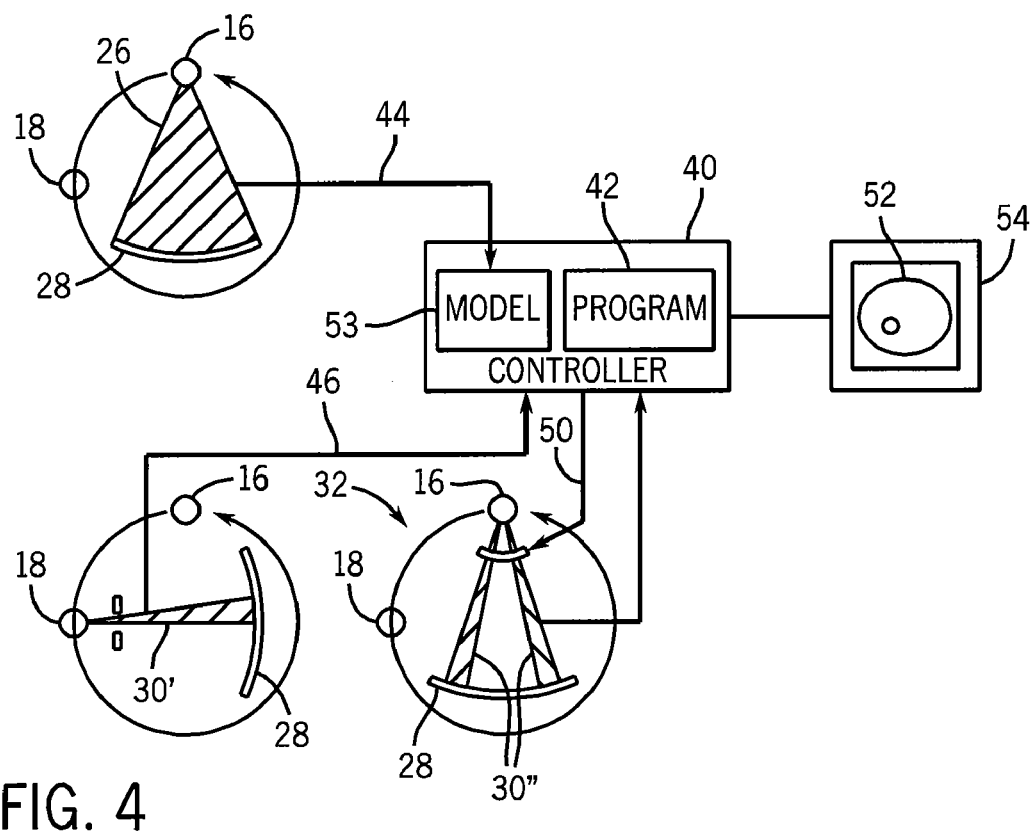
FIG. 4 is a data flow chart showing use of an acquired model of the patient and a radiation plan to provide optimized augmenting beams for enhancing image quality.

Referring now to FIG. 1, in one embodiment, a tomographic imaging system 10 may provide a rotating gantry 12 rotating about an axis 14 as shown by arrow 15. A first and second radiation source 16 and 18 may be attached to the gantry 12 to rotate within a plane perpendicular to the axis 14.

The gantry may include an open bore 20 receiving a patient supporting table 22 for positioning the patient within the plane 21 at an arbitrary location for scanning. The table 22 may be moved during rotation of the gantry 12 for so-called helical scans and the like.

Each of the radiation sources 16 and 18 may generate a radiation beam 26 directed along the plane 21 and received by a corresponding detector 28 also mounted on the gantry 12. The beam 26 may be a fan beam providing for a single plane of detection or a cone beam providing for multiple planes of detection as is understood in the art.

One of the sources 16 may be a kilovoltage source for acquiring projection data at the corresponding detector 28 for the reconstruction of a tomographic image. Generally, as will be understood in the art, a projection set provides attenuation data through the patient along a number of ray lines in the radiation beam 26 at different gantry angles over a range equal to at least the angle subtended by the ray lines plus 180 degrees.

In this case, the other radiation source 18 may be a megavoltage source for radiation treatment. In this case, the radiation source 18 may provide for a component of an IMRT machine such as is well known in the art.

It is also contemplated that both radiation sources 16 and 18 may be kilovoltage sources for dual source computed tomography or, in yet another embodiment, that there be only one source 18 used for both radiation treatment and megavoltage tomography.

Referring now to FIG. 2, the radiation beam 26 used for tomography may be divided into a series of beamlets 30 along different ray-lines. Each beamlet is defined by a shutter system 32, positioned between the radiation source 16 or 18 and detector 28, which may individually control the intensity or weight of the different beamlets 30. In the embodiment of FIG. 2, the beamlet weights are controlled by moving a radio opaque shutter, having a width in plane equal to the width of the beamlet 30, into and out of the radiation beam 26 perpendicularly to the plane 21. Changing the proportion of time during which the shutters block the beamlet 30, "duty cycle" modulates the beamlets. A shutter system suitable for this purpose is described generally in U.S. Pat. No. 5,317,616, issued May 31, 1994 and entitled: Method And Apparatus For Radiation Therapy, assigned to the assignee of the present invention and hereby incorporated by reference. In contrast to the radiation therapy application described in this patent, however, the shutter system 32 is intended to modulate imaging radiation. A similar shutter system may form part of an IMRT system that may also be part of the present invention.

Referring to FIG. 3, in an alternative embodiment the shutter system 32 may employ two or more continuously positionable collimator blades 34 movable along the plane 21 whose motion again serves to provide individual control of the weights of the different beamlets 30 according to the relative time that the beamlets 30 are un-occluded.

Referring now to FIG. 4, in a first embodiment of the invention, a controller 40 executing a stored program 42, may control the above elements of the tomographic imaging system 10 to obtain a full tomographic projection set 44 of a patient that is sufficient projection data to fully reconstruct a tomographic image of the patient. This full tomographic image provides a "forward" model 53 of the attenuating properties of the tissue of the patient along a slice through plane 21. Alternatively the forward model 53 may be derived from a tomographic scan taken on another machine or an approximation of the patient tissue properties, for example, based on standard patient anatomy.

In this embodiment, the controller 40 also receives a radiation treatment plan 46 which describes a set of weights to be used for IMRT beamlets 30 such as will be used to provide treatment to a patient. The radiation treatment plan 46 may be based on the full tomographic projection set 44, and as such, the full tomographic projection set represents a so-called planning image.

Before the radiation treatment, the controller 40 reviews the forward model 53 from the tomographic projection set 44 and the radiation treatment plan 46 to calculate an augmenting radiation plan 50. During the radiation treatment, the patient is exposed to the radiation prescribed by the radiation treatment plan (shown as beamlets 30') detected by a detector 28 and the radiation of the augmenting radiation plan 50 (shown as beamlets 30") also detected by a detector 28 to produce a combined exposure of the patient that provides improved projections data (obtained from detectors 28) for the reconstruction of a tomographic image 52 that may be displayed on output device 54. This image 52 may be used as part of an IGRT system to confirm correct dose placement. The augmenting radiation plan 50 may be implemented using a kilovoltage radiation source or megavoltage radiation source used for the IMRT. Importantly, and as will be described, the augmenting radiation plan 50 provides different beam weights for adjacent beamlets 30, specially selected to increase the image quality of the image 52 with reduced dose burden.

Figure 6:
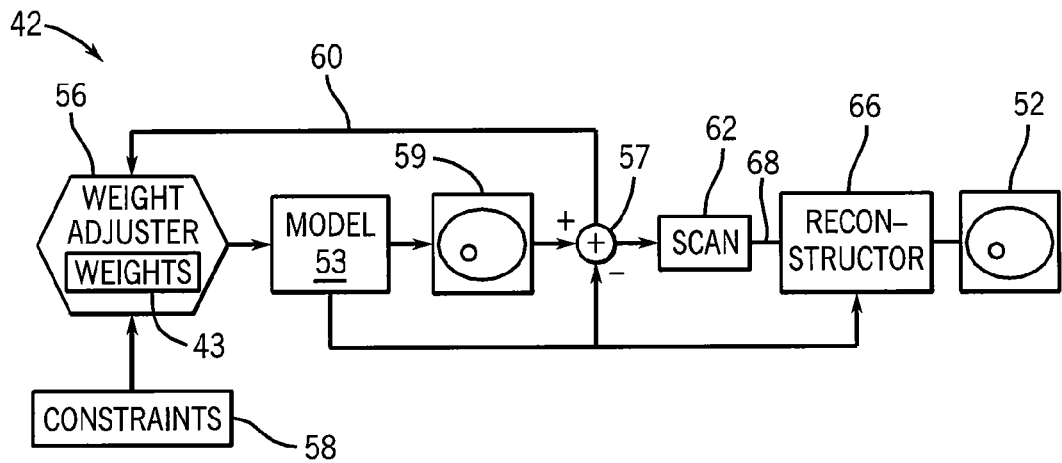
FIG. 6 is a program flow chart corresponding to the data flows of FIG. 4 or 5.

Referring now generally to FIG. 6, the program 42 produces a set of beamlet weights 43 for the augmenting radiation plan 50 by an "inverse" iterative process using a forward model 53 describing the internal structure of the patient, for example, as taken from a previous full tomographic projection set 44. The goal of the iterative process to achieve uniform imaging dose to the imaging region of interest, which is usually the area being treated plus an appropriate margin, while minimize dose outside of it. Generally the forward model 53 will not be a perfect representation of the slice or slices of the patient to be imaged, or else there would be no reason to perform the imaging, however, the process accommodates errors in the forward model 53 and, as additional images are acquired, works to reduce those errors.

The beamlet weights 43 by the "inverse" iterative process for the augmenting radiation plan 50 are selected by a weight adjuster 56, which will be described further, and which receives a set of constraints 58 being, in the embodiment of FIG. 4, the weight values of the beamlets 30 used in the radiation treatment plan 46. These weights should not be decreased, and thus constrain the weight adjuster 56 in its selection of the beamlet weights 43. Other constraints related to the limitations of the tomographic imaging system 10 may also be included.

An initial set of beamlet weights 43, within the constraints 58, is selected by the weight adjuster 56 to be an arbitrarily low set of beamlet weights 43 consistent with low dose to the patient. The beamlet weights 43 are provided to the forward model 53 and a simulated image 59 is generated. This simulated image 59 is produced by integrating the attenuation indicated by the forward model 53 along each of the paths of the beamlets 30 according to the weights or intensity of the beamlets 30. In this calculation, the beamlet weights 43 will include the weight required by the radiation treatment plan 46 plus any amount of augmenting radiation to be determined by this process.

The simulated image 59 is then compared to the forward model 53 itself at comparison block 57 and a difference value 60 is produced indicating image quality. Generally, the lower the difference value 60, the higher the quality of the image and the higher the difference value 60 the lower the quality of the image. The difference value 60 may be a straight summation of the magnitude of the differences over each pixel of the simulated image 59 and/or may be weighted according to the structure of particular interest or the absolute amount of the differences.

If the difference value 60 is greater than desired (based on a predetermined target image quality) then the program 42 returns to the weight adjuster 56 and new beam weights are selected within the constraints 58. The modification of the beamlet weights 43 may be according to any number of well-known algorithms including simulated annealing or genetic algorithms that incrementally move the beam weights upward until the desired dose is achieved.

This process of adjusting beamlet weights 43, modeling them and checking the difference may be repeated for a number of iterations until the difference value 60 drops to an acceptable level. At this time the program 42 proceeds to an actual scan 62 and the beamlet weights 43 are used to control a shutter system 32 on the megavoltage source or the megavoltage source and a separate kilovoltage source to obtain scan projection data 68.

The resulting scan projection data 68 (possibly being a combination of multiple sources 16 and 18) is provided to an image reconstructor 66 which produces an image 52. This image 52 may be displayed and may serve as a model for determining additional beamlet weights 43 for a next scan.

Figure 7:
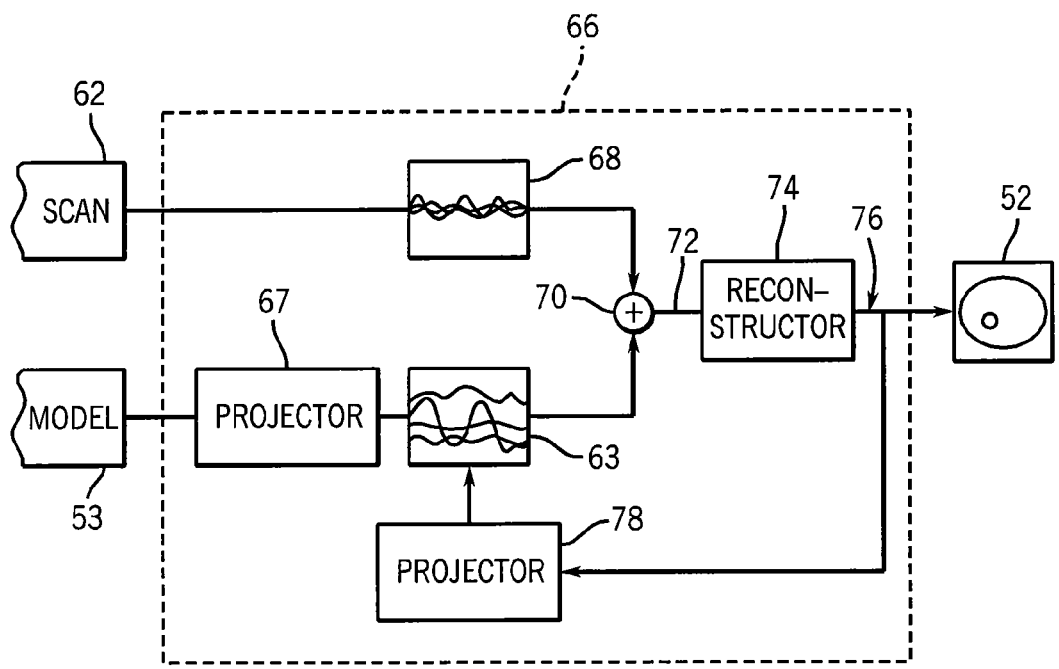
FIG. 7 is a detailed program flow chart of the imaging step of FIG. 6.

Referring now to FIG. 7, in a further embodiment, the image reconstructor 66 may take the scan projection data 68 from the scan 62, such as generally represents an attenuation sinogram, and may further process it to supplement those projections (e.g., attenuation data from particular beamlets 30 at a particular gantry angles) which were associated with low or zero beam weights. This may be done, for example, by a combiner 70 that combines the scan projection data 68 obtained from the scan 62 with data from the forward model 53, reprojected by reprojector 67, to form model projection data 63. Generally the combiner 70 splices in projections from the model projection data 63 according to what data is missing from scan projection data 68.

When scan projection data 68 is obtained with a binary switching of the shutters for example, with beamlet weights 43 that are either at zero or 100 percent, the combiner 70 simply takes the projections from the model projection data 63 to fill in the missing projections of scan projection data 68.

Where scan projection data 68 includes continuously varying beam weights, then a weighting function is adopted to combine the scan projection data 68 with the model projection data 63. Thus for example if a beamlet 30 at a given projection is operating at 20% of maximum intensity, then 20% of the value of that projection in the scan projection data 68 is combined with 80% of the value of the corresponding projection in the model projection data 63.

The combined data set 72 from the combiner 70 is provided to reconstructor 74, for example, one that uses filtered back projection, to produce an interim image 76.

This interim image 76 is then reprojected by reprojector 78 to turn it back into sinogram data which replaces the model projection data 63. This process of combining and reprojecting is repeated iteratively. After a number of iterations that may be determined empirically, an output image 52 is provided.

Figure 5:
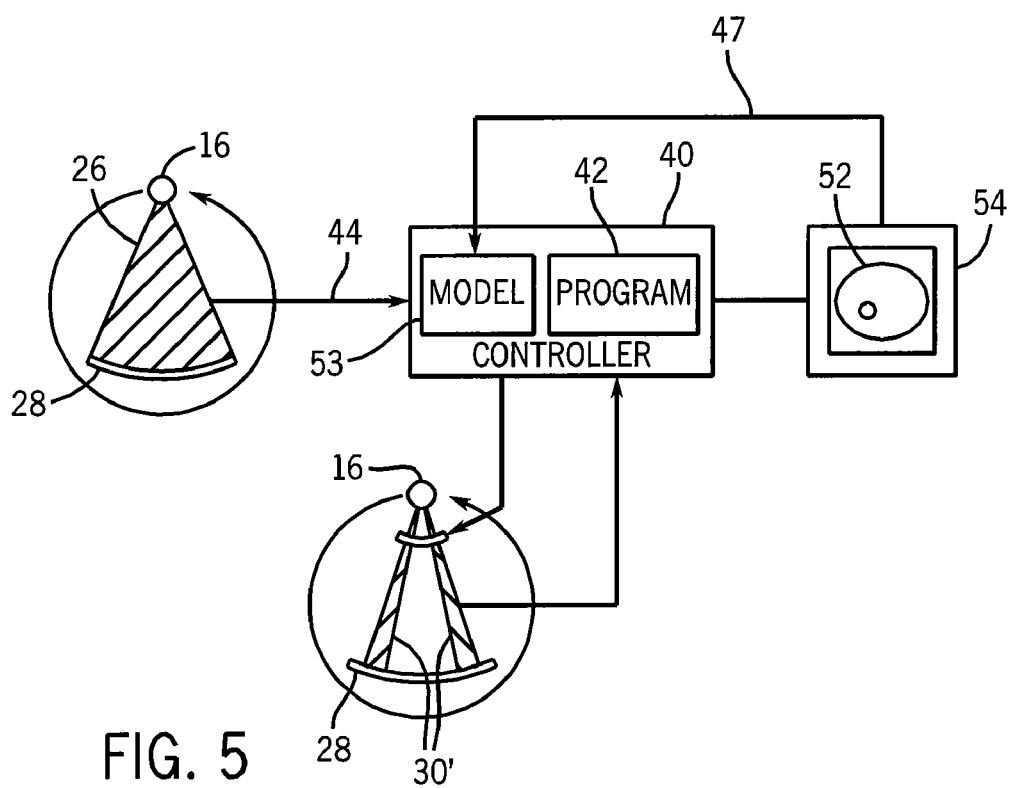
FIG. 5 is a figure similar to that of FIG. 4 showing an alternative embodiment not using a radiation plan and suitable for stand-alone CT systems.

Referring to FIG. 5, this invention may also be used outside of the radiation therapy context for a CT machine that provides for a reduced dose to the patient. In this case, the tomographic projection set 44, for example, a first frame of a cinematographic sequence, provides for the model 53 which is used to optimize the beamlet weights 43 used for subsequent images to provide reduced dose at the desired image quality. As each frame is acquired the data of the acquired image may become the new model 53 as indicated by arrow 47.

When the above invention is used on a kilovoltage CT system, the shutter system may be much lighter and more easily constructed than the shutter used in radiotherapy.

It is specifically intended that the present invention not be limited to the embodiments and illustrations contained herein, but include modified forms of those embodiments including portions of the embodiments and combinations of elements of different embodiments as come within the scope of the following claims.

What we claim is:

1. A computed tomography imaging machine comprising:
    a radiation source (16, 18) providing a radiation beam divisible into regions (30) being individually controllable in intensity;
    a radiation detector (28) for detecting the radiation from the radiation beam to produce attenuation signals;
    a patient support (22) supporting a patient between the radiation source and radiation detector; and
    a controller (40) holding a stored model (53) of the patient and controlling the intensities of the radiation beam in the different regions based on a contribution (60) by the radiation of the regions to a quality of a tomographic image as determined from the stored model.

2. The computed tomography imaging machine of claim 1 wherein calculation of the intensity of the radiation beam in the different regions is performed by an inverse calculation in which intensities (43) are iteratively modified (56) based on a comparison of a calculated image (59) using the intensities applied to the stored model (53) in comparison (57) to the stored model itself.

3. The computed tomography imaging machine of claim 1 wherein the intensity of the radiation beam in the regions is controlled to reduce dose to the patient for a given image quality.

4. The computed tomography imaging machine of claim 1 wherein the stored model is a tomographic image (44) of the patient.

5. The computed tomography imaging machine of claim 4 wherein the tomographic image is a previous image of the patient provided by the computed tomography imaging machine.

6. The computed tomography imaging machine of claim 5 wherein the previous image is obtained when the controller is controlling the intensity of the regions of the radiation beam.

7. The computed tomography imaging machine of claim 1 wherein the radiation source is selected from the group consisting of kilovoltage x-ray sources and megavoltage x-ray sources.

8. The computed tomography imaging machine of claim 1 wherein the radiation source includes a multi-leaf collimator (32) providing a plurality of leaves moving into and out of the radiation beam to control the intensity within the regions, wherein at least one leaf is associated with each region.

9. The computed tomography machine of claim 1 wherein the radiation source includes opposing shutter blades (34) moving across multiple regions to control the intensity within the regions.

10. The computed tomography imaging machine of claim 1 wherein the controller controls the intensity of the radiation beams in the regions assuming a subset (58) of regions of predetermined intensity.

11. The computed tomography imaging machine of claim 10 wherein the subset of regions of given intensity are obtained from a radiation therapy treatment plan.

12. The computed tomography imaging machine of claim 1 wherein the intensities are controlled to only an on or off state.

13. The computed tomography imaging machine of claim 1 wherein the intensities are controlled among a range of intensity values.

14. The computed tomography imaging machine of claim 1 wherein the computed tomography imaging machine includes multiple radiation sources (16, 18) and wherein the radiation beam is provided by no less than one radiation source.

15. The computed tomography imaging machine of claim 1 wherein the controller further reconstructs (66) a tomographic image from the attenuation signals from the controlled intensity radiation beams (68) after augmenting (70) the attenuation signals with information from the model (63).

16. A method of low dose tomographic imaging comprising:
    (a) providing a stored model (53) of a patient being imaged;
    (b) based on the stored model, controlling intensities of different of regions (30) within a radiation beam directed toward the patient (62) based on a calculated contribution (57) by the radiation of the regions to a quality of a tomographic image of the patient; and (c) reconstructing (66) an image of the patient using attenuation data collected at a detector (28) receiving the radiation beam after passage through the patient.

17. The method of claim 16 wherein the intensities of the different regions are determined by inverse modeling (56, 53, 59, 57, 60) of beam intensities based on the model.

18. The method of claim 16 wherein the intensities of the radiation beam in the regions are controlled to reduce dose to the patient for a given image quality.

19. The method of claim 16 wherein the stored model is a tomographic image (44) of the patient.

20. The method of claim 19 including the step of acquiring a series of multiple images and wherein the tomographic image is a previous image of the patient in the series.

21. The method of claim 20 wherein the previous image is obtained while controlling intensities of different of regions.

22. The method of claim 16 wherein the radiation beam is of an energy selected from the group consisting of: kilovoltage x-rays and megavoltage x-ray sources.

23. The method of claim 16 wherein the step of controlling intensities assumes predetermined intensities (58) for a subset of the regions.

24. The method of claim 23 wherein the subset of regions of given intensity are obtained from a radiation therapy treatment plan.

25. The method of claim 16 wherein the intensities are controlled to on or off states.

26. The method of claim 16 wherein the intensities are controlled among a range of values.

27. The method of claim 16 wherein the step of reconstructing (66) reconstructs a tomographic image from the attenuation data after augmenting (70) the attenuation data with information from the stored model.

* * * * *